US00PP23004P2

(12) United States Plant Patent
Zaiger et al.

(10) Patent No.: US PP23,004 P2
(45) Date of Patent: Sep. 4, 2012

(54) PEACH TREE NAMED 'KODIAK'

(50) Latin Name: *Prunus persica*
Varietal Denomination: Kodiak

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/068,419

(22) Filed: May 11, 2011

(51) Int. Cl.
*A01H 5/00* (2006.01)

(52) U.S. Cl. ..... Plt./195

(58) Field of Classification Search ..... Plt./195
See application file for complete search history.

*Primary Examiner* — Annette Para

(57) ABSTRACT

A new and distinct variety of peach (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous upright growth.
2. The tree being a regular and productive bearer of large size fruit.
3. Fruit with a mild, sweet, low acid flavor and very good eating quality.
4. Fruit having a high degree of attractive red skin color.
5. Fruit with good storage and shipping quality.

1 Drawing Sheet

Botanical classification: *Prunus persica.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach tree, which are known to us, and mentioned herein, 'Sugar Lady' Peach (U.S. Plant Pat. No. 7,532), 'Rich Lady' Peach (U.S. Plant Pat. No. 7,290), 'Country Sweet' Peach (U.S. Plant Pat. No. 11,090), 'Earlitreat' Peach (U.S. Plant Pat. No. 9,842), 'Spring Snow' Peach (U.S. Plant Pat. No. 9,883) and our proprietary peach seedling selections with the field identification numbers '92ED535' and '36ZD906'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from seed of an open pollinated proprietary seedling with the field identification number '36ZD906'. The seed parent (36ZD906) originated from crosses between 'Sugar Lady' Peach (U.S. Plant Pat. No. 7,532), 'Rich Lady' Peach (U.S. Plant Pat. No. 7,290), 'Country Sweet' Peach (U.S. Plant Pat. No. 11,090), 'Earlitreat' Peach (U.S. Plant Pat. No. 9,842) and the proprietary peach seedling with the field identification number '92ED535'. A large group of these open pollinated seedlings were planted and maintained on their own root systems, during which time we recognized the desirable tree and fruit characteristics of the present seedling and selected it in 2004 for additional asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a productive and regular bearer of large size, white flesh, clingstone fruit with mild, sweet, low-acid flavor and very good eating quality. The fruit is further characterized by having attractive red skin blush with good handling and storage ability. In comparison to its immediate seed parent (36ZD906) the fruit of the new variety is larger in size, has more attractive skin color and is approximately 14 days later in maturity. In comparison to the commercial variety 'Spring Snow' Peach (U.S. Plant Pat. No. 9,883) the fruit of the new variety is firmer and is approximately 8 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 6 year old specimens grown near Modesto, Calif., with color in accordance with Munsell Book of Color.

Tree:

*Size*.—Large, normally pruned to 3 to 3.5 meters in height and width for economical harvesting of fruit.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size.

*Bearer*.—Regular, adequate fruit set 4 consecutive years. No alternate bearing observed.

*Fertility*.—Self-fertile.

*Density*.—Medium dense, usually pruned to vase shape to allow more sunlight to center of tree to enhance fruit color and health of fruit wood.

*Hardiness*.—Hardy in all stone fruit growing areas of California. Tree grown in USDA Hardiness Zone 9. Winter chilling requirement approximately 700 hours at or below 45° F.

Trunk:

*Size*.—Large. Average circumference 52.1 cm at 23 cm above ground on a 6 year old tree.

*Stocky*.—Medium stocky.

*Texture*.—Medium shaggy, roughness increases with age.

*Color*.—Varies from 10YR 3/2 to 2.5Y 3/4.

Branches:

*Size*.—Medium. Average circumference 15.2 cm at 1.2 meters above ground. Crotch angle approximately 35°, increases with crop load.

*Surface texture*.—New growth relatively smooth. Mature growth medium rough, roughness increases with age.

*Lenticels*.—Average number 19 in a 25.8 square cm area. Average length 5.9 mm. Average width 2.2 mm. Color varies from 7.5YR 6/10 to 10YR 6/8.

*Color*.—New growth varies from 5GY 6/6 to 5R 3/8 where exposed to the sun. Mature growth varies from 10YR 3/4 to 2.5Y 4/4, varies with age of growth.

Leaves:

*Size*.—Medium to large. Average length 138.0 mm. Average width 43.7 mm.

*Form*.—Lanceolate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins. Lower surface relatively smooth, small ridges created by midrib and pinnate venation. Both surfaces glabrous.

*Petiole*.—Average length 10.4 mm. Average width 1.7 mm. Longitudinally grooved. Surface glabrous. Color varies from 5GY 4/6 to 5GY 4/8.

*Glands*.—Type — reniform. Size — small to medium. Average length 1.2 mm. Average diameter 1.0 mm. Number varies from 2 to 4, average number 3. Located primarily on the base of the leaf blade and the upper portion of the petiole. Color varies from 5GY 6/6 to 5GY 5/6.

*Stipules*.—Average number 2. Average length 10.7 mm. Margin — pectinate. Color varies from 5GY 7/6 to 5GY 5/6.

*Color*.—Upper surface varies from 5GY 3/6 to 7.5GY 3/6. Lower surface varies from 5GY 4/6 to 7.5GY 4/4. Midvein color varies from 2.5GY 8/6 to 2.5GY 7/6.

Flower buds:

*Size*.—Medium to large. Average length 19.2 mm. Average diameter 11.4 mm.

*Hardiness*.—Hardy with respect to California winters.

*Form*.—Conical, becomes elongated before opening.

*Pedicel*.—Average length 4.8 mm. Average width 1.6 mm. Color varies from 2.5GY 4/6 to 5GY 5/6.

*Color*.—Varies from 5RP 7/8 to 7.5RP 6/12.

Flowers:

*Blooming period*.—Date of First Bloom Feb. 19, 2010. Date of Petal Fall Mar. 1, 2010, varies slightly with climatic conditions.

*Size*.—Large, showy. Average height 21.0 mm. Average diameter 41.6 mm.

*Petals*.—Size — large. Number — normally 5, alternately arranged to sepals. Average length 21.1 mm. Average width 21.3 mm. Form — globose. Margin — sinuate, slightly cupped. Color varies from 5RP 8/4 to 5RP 7/6, fades with age of flower. Both surfaces glabrous.

*Sepals*.—Size — large. Number — normally 5, alternately arranged to petals. Average length 7.3 mm. Average width 6.4 mm. Form — ovate, apex rounded. Margin — entire. Color — upper surface varies from 2.5GY 4/6 to 5R 3/4. Lower surface varies from 5R 5/4 to 7.5R 2/4. Upper surface glabrous, lower surface pubescent.

*Stamens*.—Average number per flower 44. Average filament length 15.3 mm. Filament color varies from 5RP 9/2 to 2.5RP 7/6. Anther color varies from 10R 4/10 to 5Y 8/8.

*Pollen*.—Self fertile. Color varies from 2.5Y 7/12 to 5Y 7/10.

*Pistil*.—Normally one. Surface pubescent. Average length 19.3 mm. Position of stigma — even in height with anthers. Color varies from 10Y 7/6 to 2.5GY 7/6.

*Fragrance*.—Heavy aroma.

*Color*.—Varies from 2.5RP 8/6 to 5RP 8/6.

*Number flowers per flower bud*.—Normally one.

*Pedicel*.—Average length 5.7 mm. Average width 1.7 mm. Color varies from 2.5GY 4/6 to 10R 2/4.

Fruit:

*Maturity when described*.—Firm ripe.

*Date of first picking*.—Jun. 3, 2010.

*Date of last picking*.—Jun. 10, 2010, varies slightly with climatic conditions.

*Size*.—Large. Average diameter axially 68.1 mm. Average transversely in suture plane 71.2 mm. Average weight 181.8 grams, average weight varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Rounded to very slight tip.

*Base*.—Retuse.

*Stem cavity*.—Rounded to slightly elongated in the suture plane. Average depth 6.7 mm. Average diameter 9.6 mm.

Stem:

*Size*.—Small to medium. Average length 8.4 mm. Average diameter 3.8 mm.

*Color*.—Varies from 2.5GY 6/6 to 2.5GY 5/8.

Flesh:

*Ripens*.—Evenly.

*Texture*.—Firm and meaty.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Very good, mild and sweet, low acid.

*Juice*.—Moderate amount, enhances flavor.

*Brix*.—Average 14.0°, varies slightly with amount of fruit per tree and climatic conditions.

*Color*.—Varies from 5Y 9/1 to 7.5Y 9/2. Pit cavity varies from 5Y 7/4 to 7.5Y 7/4.

*Pit cavity*.—Average length 38.6 mm. Average width 27.7 mm.

Skin:

*Thickness*.—Medium.

*Surface*.—Smooth to slightly waffled.

*Pubescence*.—Moderate amount.

*Tendency to crack*.—None.

*Color*.—Ground color varies from 7.5Y 8/2 to 10Y 7/2. Overspread with 7.5R 4/8 to 7.5R 3/6.

*Tenacity*.—Tenacious to flesh.

*Astringency*.—Undetected.

Stone:

*Type*.—Clingstone.

*Size*.—Large. Average length 37.1 mm. Average width 26.0 mm. Average thickness 18.1 mm.

*Form*.—Ovoid.

*Base*.—Varies from flat to slightly rounded.

*Apex*.—Pointed. Average length 3.8 mm.

*Surface*.—Pitted throughout, pits vary from round to elongated.

*Sides*.—Unequal, one side extending further from the suture plane.

*Ridges*.—Relatively smooth, extending from base to apex.

*Tendency to split*.—None.

*Color*.—Varies from 7.5YR 6/4 to 7.5YR 6/6 when dry.

Kernel:

*Size*.—Medium to large. Average length 19.4 mm. Average width 11.0 mm. Average depth 6.7 mm.

*Form*.—Ovate.

*Viability*.—Non-viable, incomplete embryo development.

*Skin*.—Color varies from 5Y 9/2 to 5Y 9/4.

Use: Dessert.

*Market*.—Local and long distance.

Keeping quality: Good, held firm in cold storage at 38° to 42° F. for 2 weeks without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, substantially as illustrated and described.

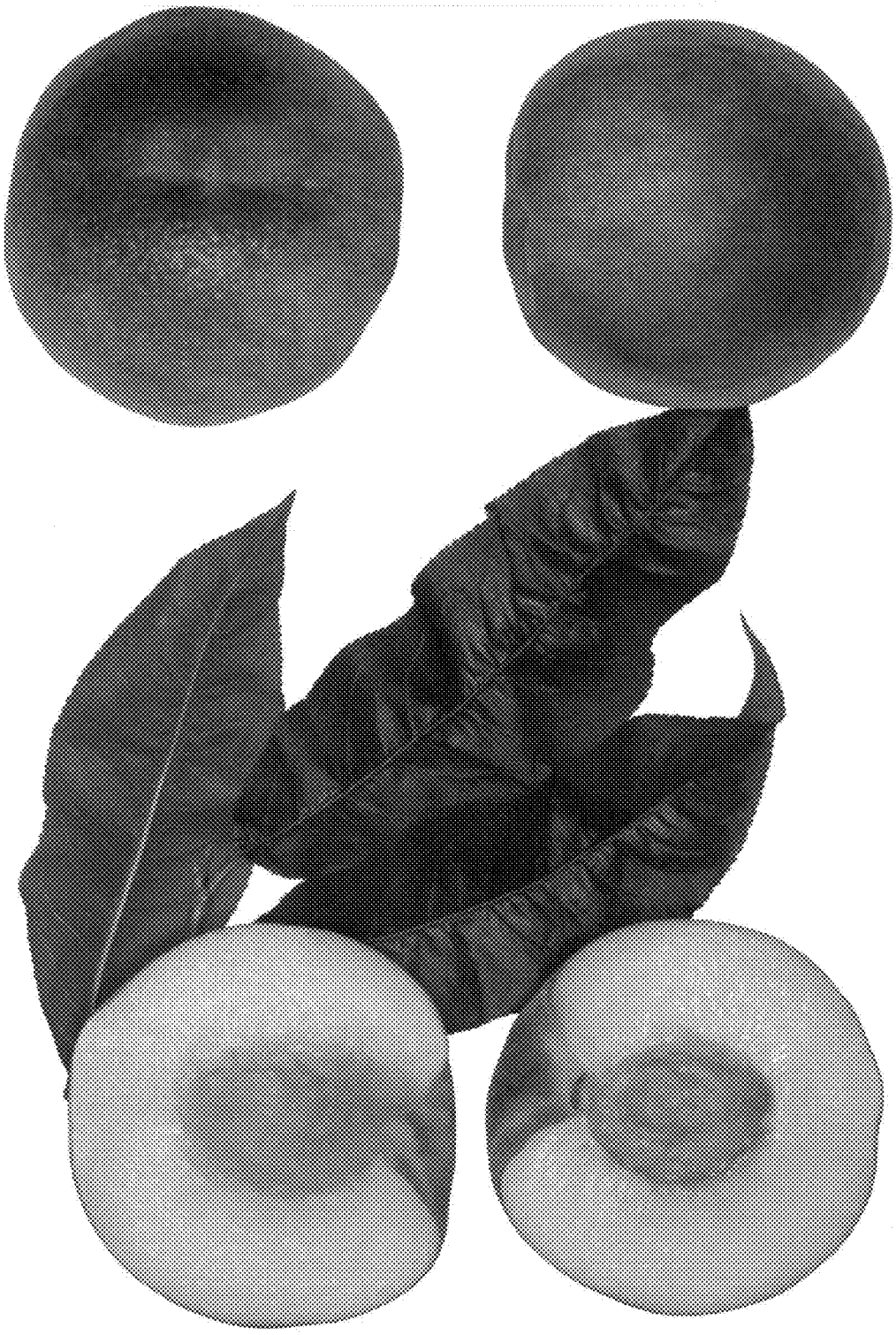

* * * * *